United States Patent
Nara et al.

(10) Patent No.: US 11,495,331 B2
(45) Date of Patent: Nov. 8, 2022

(54) DOCUMENT CREATION ASSISTANCE SERVER AND DOCUMENT CREATION ASSISTANCE METHOD

(71) Applicants: TAKEDA PHARMACEUTICAL COMPANY LIMITED, Osaka (JP); PATCORE, INC., Tokyo (JP)

(72) Inventors: Hiroshi Nara, Fujisawa (JP); Junya Shirai, Fujisawa (JP); Tatsuki Koike, Fujisawa (JP); Kenjiro Sato, Fujisawa (JP); Takaharu Hirayama, Fujisawa (JP); Hiromi Fukuda, Fujisawa (JP); Tsutomu Morita, Fujisawa (JP); Hiromasa Ishihara, Fujisawa (JP); Kazue Suzuki, Fujisawa (JP); Hiroki Sakamoto, Fujisawa (JP); Fumiaki Kikuchi, Fujisawa (JP); Kenta Tamaki, Tokyo (JP); Toru Tanoue, Fukuoka (JP); Yuichi Horita, Fukuoka (JP); Takeshi Ueda, Osaka (JP)

(73) Assignees: TAKEDA PHARMACEUTICAL COMPANY LIMITED, Osaka (JP); PATCORE, INC., Tokyo (JP)

( * ) Notice: Subject to any disclaimer, the term of this patent is extended or adjusted under 35 U.S.C. 154(b) by 362 days.

(21) Appl. No.: 16/766,559

(22) PCT Filed: Sep. 10, 2018

(86) PCT No.: PCT/JP2018/033383
§ 371 (c)(1),
(2) Date: May 22, 2020

(87) PCT Pub. No.: WO2019/102687
PCT Pub. Date: May 31, 2019

(65) Prior Publication Data
US 2020/0388354 A1   Dec. 10, 2020

(30) Foreign Application Priority Data

Nov. 27, 2017   (JP) .............................. JP2017-226890

(51) Int. Cl.
*G16H 15/00*   (2018.01)
*G16C 20/80*   (2019.01)
*G16C 20/10*   (2019.01)

(52) U.S. Cl.
CPC ............. *G16C 20/10* (2019.02); *G16C 20/80* (2019.02); *G16H 15/00* (2018.01)

(58) Field of Classification Search
None
See application file for complete search history.

(56) References Cited

U.S. PATENT DOCUMENTS

| 6,088,629 A | 7/2000 | Tomonaga et al. |
| 7,250,950 B2 * | 7/2007 | Smith .................... G16C 20/10 345/440 |
| 2007/0208800 A1 | 9/2007 | Frohlich et al. |

FOREIGN PATENT DOCUMENTS

| EP | 1276059 A2 * | 1/2003 | ........... G06F 16/332 |
| JP | 09-138808 A | 5/1997 | |

(Continued)

OTHER PUBLICATIONS

International Search Report and Written Opinion dated Nov. 27, 2018 corresponding to International Patent Application No. PCT/JP2018/033383, and English translation thereof.

*Primary Examiner* — Kristy A Haupt
(74) *Attorney, Agent, or Firm* — Squire Patton Boggs (US) LLP

(57) ABSTRACT

An objective of the present invention is to provide a document creation assistance server and document creation assistance method which are capable of efficiently acquiring information necessary to write a specification or other such (Continued)

documents, and of generating a document from the acquired information. According to an embodiment, this document creation assistance server for assisting with the creation of a document comprises: a final product identification part for accepting identification information for identifying a final product generated by synthesizing a plurality of chemical compounds; a chemical equation acquisition part for referring to electronic experiment note data which provides an electronic record of the details of an experiment relating to the synthesis of the chemical compounds, and acquiring a chemical equation for generating the final product associated with the accepted identification information; and a document generation part for generating a document including the acquired chemical equation.

12 Claims, 13 Drawing Sheets

(56) References Cited

FOREIGN PATENT DOCUMENTS

| JP | 2000-099537 A | | 4/2000 | | |
|---|---|---|---|---|---|
| JP | 2000099537 A | * | 4/2000 | | |
| JP | 2007-149087 A | | 6/2007 | | |
| JP | 2008-516351 A | | 5/2008 | | |
| JP | 2009-080645 A | | 4/2009 | | |
| WO | WO-2006040134 A1 | * | 4/2006 | ........... | G06F 21/602 |

* cited by examiner

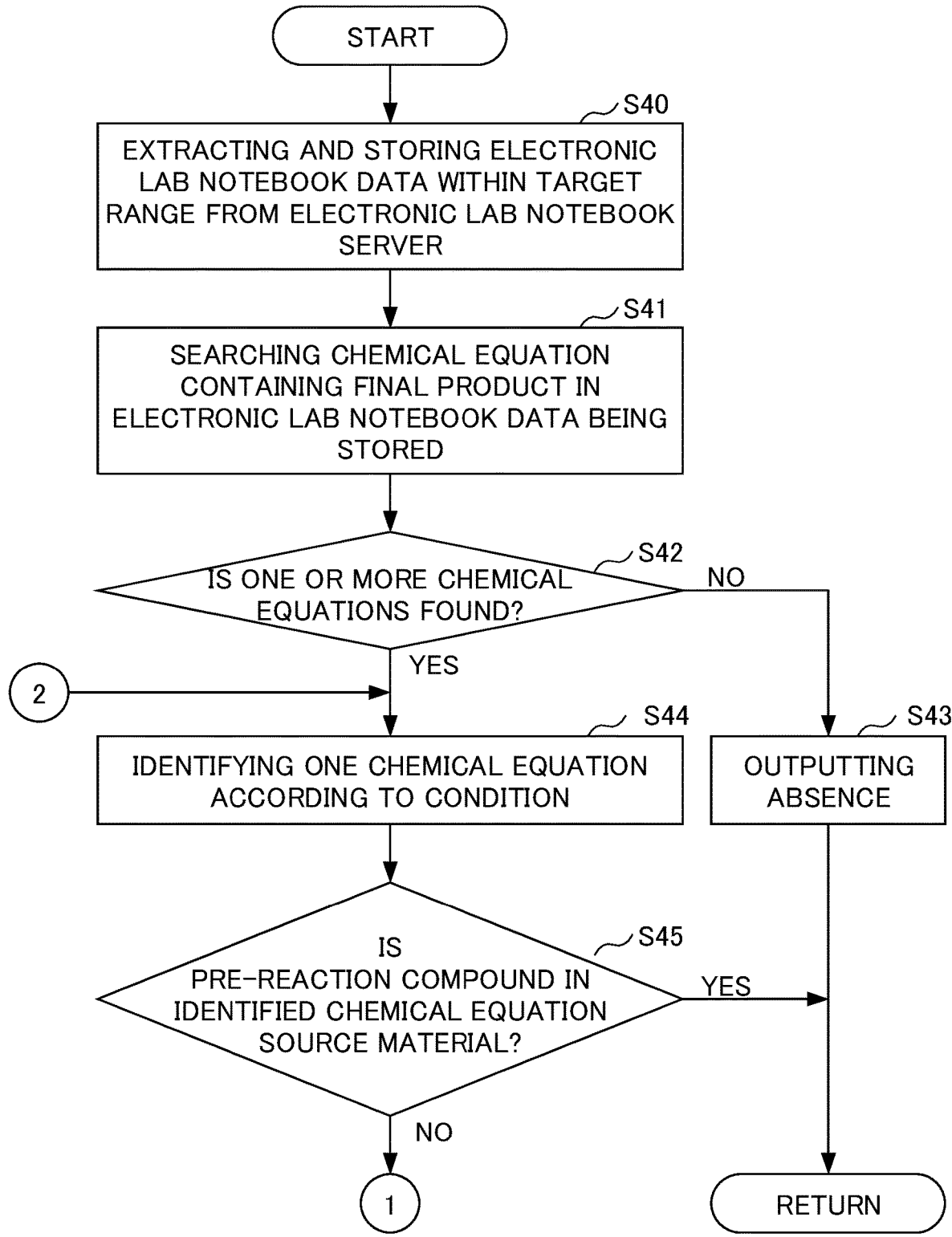

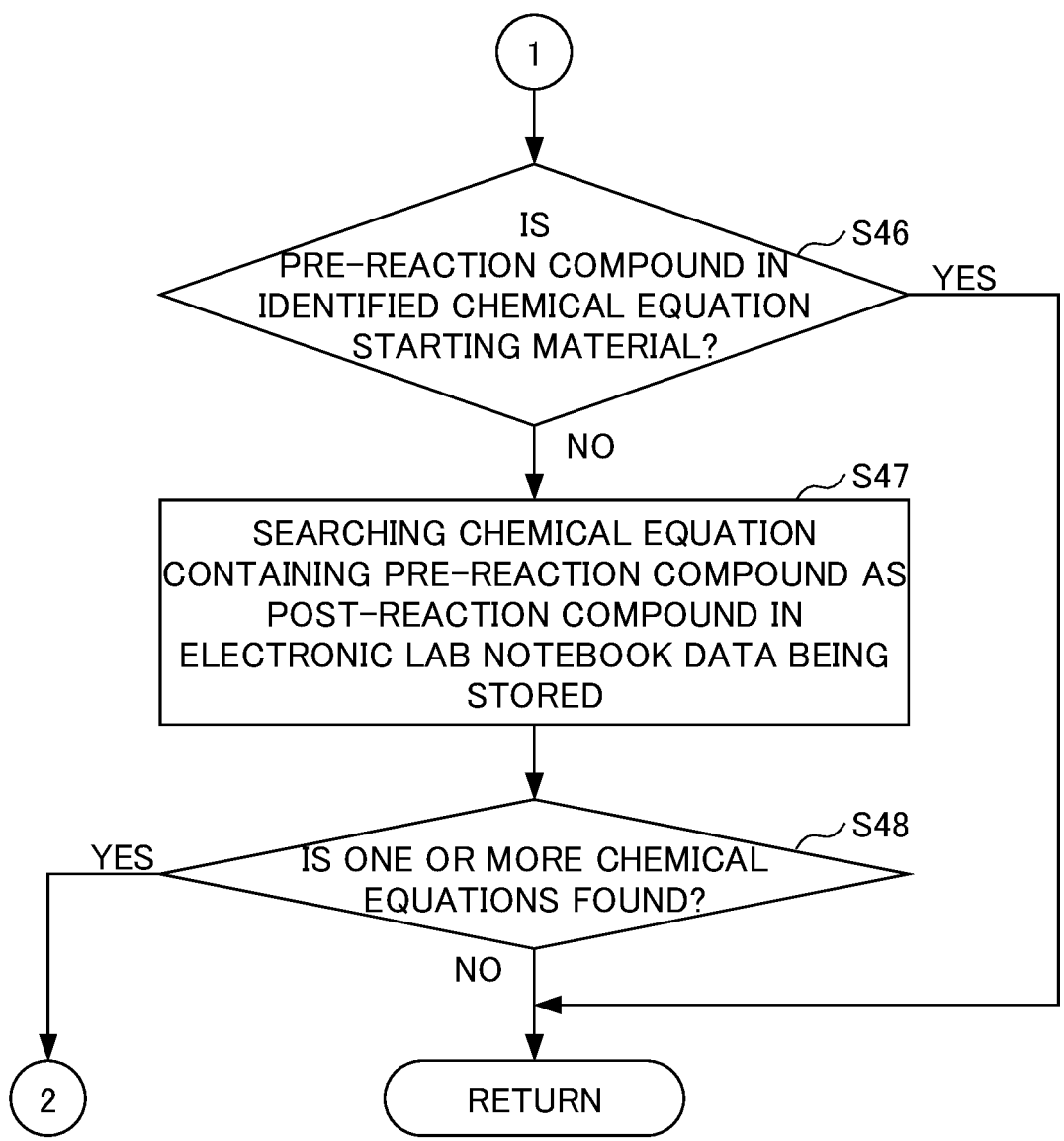

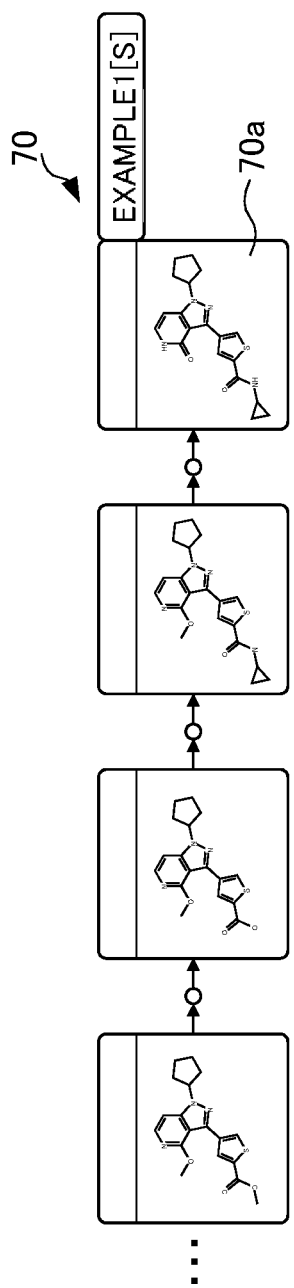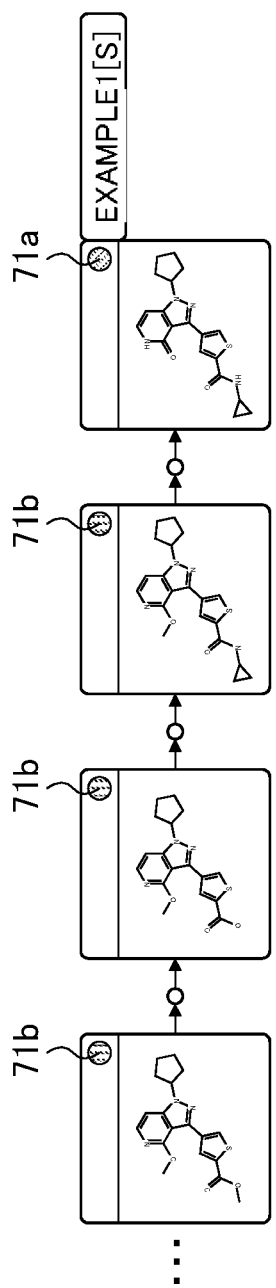

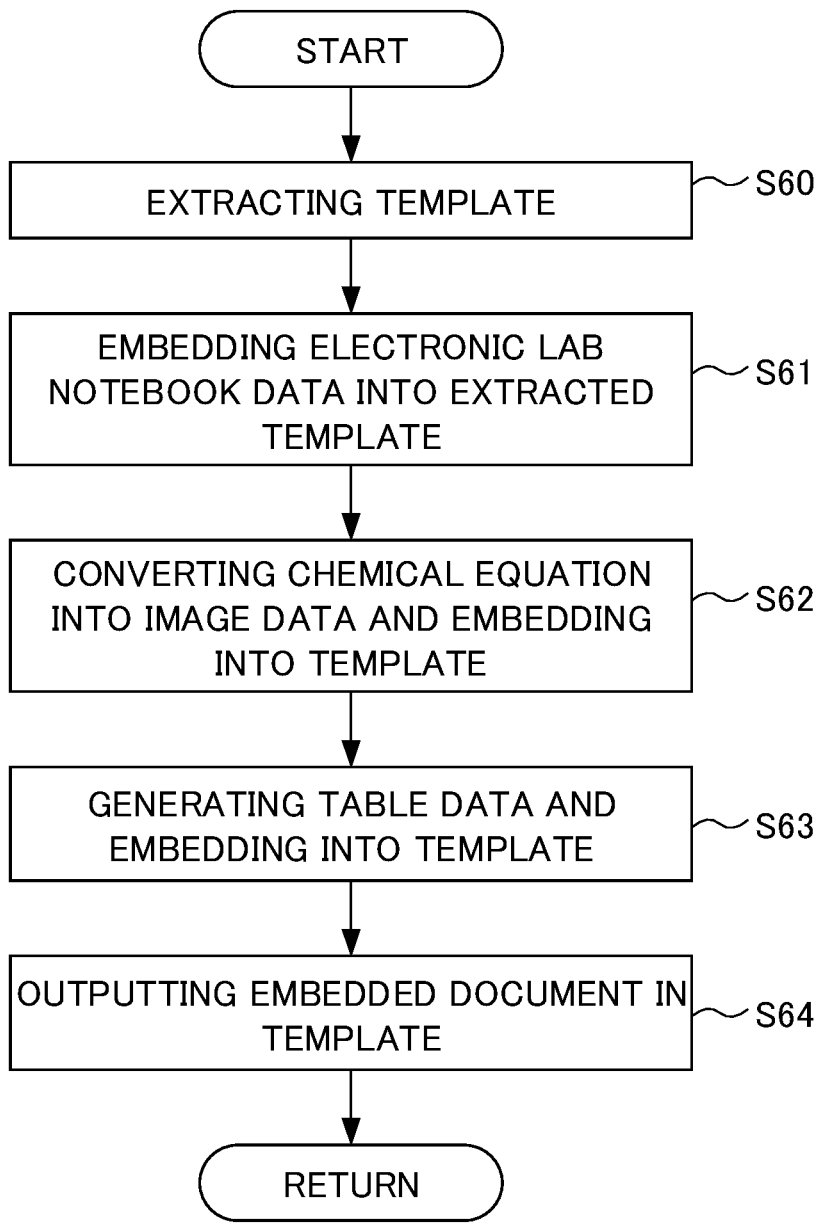

FIG. 10

DOCUMENT DATA 82

The present invention is described in further detail with reference to Examples, test examples, and formulation example; however, the present invention is not in any way limited thereto and modifications may be made within the range not to depart from the scope of the present invention.
In Examples below, "room temperature" generally means a temperature from about 10°C to 35°C. The ratio specified for a mixed solvent means a capacity ratio unless otherwise noted. The percentage means % by weight unless otherwise noted.
The elution by column chromatography in Example ...
· · · · · ·

The following abbreviations are used in the following Examples.
mp: melting point   MS: mass spectrum   M: molar concentration   N: normality
· · · · · ·

EXAMPLE 1
To a mixture of 4-(1-cyclopentyl-4-oxo-4,5-dihydro-1H-pyrazolo[4,3-c]pyridine-3-yl)-N-cyclopropylthiophene-2-carboxamide

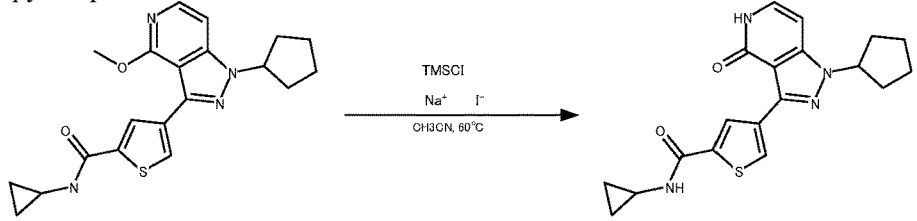

4-(1-cyclopentyl-4-methoxy-1H-pyrazolo[4,3-c]pyridine-3-yl)-N-cyclopropylthiophene-2-carboxamide (68. 4 mg) and $CH_3CH$ (10 mL), sodium iodide (53. 6 mg) and TMSCl (155 mg) were added at room temperature. The mixture thus obtained was stirred at 60°C for 30 minutes. When the temperature dropped to room temperature, water was added and extraction with ethyl acetate was carried out. After separation of an organic layer, washing with saturated saline solution, drying with anhydrous sodium sulfate, and vacuum concentration were carried out. The residue was purified by silica gel column chromatography (ethyl acetate/hexane 80%-100%) and then washed with 1:1 ethyl acetate/IPE, to give light yellow solid of the specified compound (56. 8 mg).
1H NMR (300 MHz, DMSO-d6) δ 0.53 - 0.79 (4 H, m), 1.56 - 1.80 (2 H, m), 1.82 - 2.23 (6 H, m), 2.82 (1 H, tq, J=7.3, 3.9 Hz), 5.02 (1 H, quin, J=7.4 Hz), 6.67 (1 H, d, J=7.2 Hz), 7.08 - 7.35 (1 H, m), 8.28 (1 H, s), 8.68 (1 H, d, J=3.8 Hz), 9.16 (1 H, s), 11.12 (1 H, d, J=5.7 Hz); MS m/z 369.1 [M+H]+.

The compounds of Examples are shown in Table below. In Table, MS indicates an actual measured value. The compound of Example 5 in Table was produced according to the procedure described above in the embodiment or a similar procedure.

| EXAMPLE NUMBER | IUPAC NAME | STRUCTURAL FORMULA | SALT | MS |
|---|---|---|---|---|
| 1 | 4-(1-cyclopentyl-4-oxo-4,5-dihydro-1H-pyrazolo[4,3-c]pyridine-3-yl)-N-cyclopropylthiophene-2-carboxamide | | | 369. 1 |

DOCUMENT CREATION ASSISTANCE SERVER AND DOCUMENT CREATION ASSISTANCE METHOD

TECHNICAL FIELD

The present invention relates to a document creation assistance server and a document creation assistance method.

BACKGROUND ART

Conventionally, for example in a pharmaceutical company, a chemist synthesizes a compound, i.e., a novel chemical substance, and carries out experiments for determining medicinal effects of the compound on a daily basis. The chemist describes the experiments on a lab notebook. Such a lab notebook once was made of paper; however, an electronic lab notebook is used in recent years (see, for example, Patent Document 1). After the experiments, a compound proven to have medicinal effects is subjected to a patent application in order to obtain the right for the substance. Upon filing of a patent application, documents such as a specification must be drafted. For example, a document creation assistance device that assists with creation of a document for patent application is disclosed (see, for example, Patent Document 2).

Patent Document 1: Japanese Unexamined Patent Application (Translation of PCT Application), Publication No. 2008-516351

Patent Document 2: Japanese Unexamined Patent Application, Publication No. 2007-149087

DISCLOSURE OF THE INVENTION

Problems to be Solved by the Invention

In a specification of a patent application related to a compound, all compounds generated in the course of synthesis must be specified in the order of synthesis. However, since there are various synthesis pathways and the lab notebook includes an enormous amount of data, it has been cumbersome to identify the adequate synthesis pathway from the lab notebook. In this regard, efficient acquisition of information required for drafting an experiment example in a specification etc. has been awaited.

An object of the present invention is to provide a document creation assistance server and a document creation assistance method that enable efficient acquisition of information required for drafting a specification etc., and generation of a document on the basis of the information thus obtained.

Means for Solving the Problems

According to a first aspect of the present invention, a document creation assistance server (1) for assisting with creation of a document that serves as an Example, includes: an identification information accepting means (12) that accepts identification information that identifies a final product generated through synthesis of a plurality of compounds; a chemical equation obtaining means (14) that obtains a chemical equation for generating the final product corresponding to the identification information accepted by the identification information accepting means, with reference to electronic lab notebook data that electrically describes experiments related to the synthesis of the compounds; and a document generating means (17) that generates a document containing the chemical equation obtained by the chemical equation obtaining means.

According to a second aspect of the present invention, in the document creation assistance server (1) according to the first aspect, the chemical equation obtaining means (14) may obtain the chemical equation included in a synthesis pathway between a source material and the final product.

According to a third aspect of the present invention, the document creation assistance server (1) according to the first or second aspect may further include a condition accepting means (13) that accepts a condition for obtaining the chemical equation, in which the chemical equation obtaining means (14) may obtain the chemical equation according to the condition. According to a fourth aspect of the present invention, in the document creation assistance server (1) according to the third aspect, the condition may relate to at least one of: yield; yielded amount; chemist responsible for synthesis; and the number of compounds included in the synthesis pathway. According to a fifth aspect of the present invention, the document creation assistance server (1) according to any one of the first to fourth aspects may further include: an editing means (15) that edits the compound included in the chemical equation obtained by the chemical equation obtaining means (14), so as to correspond to a nature of the compound; and a chemical equation outputting means (16) that outputs a chemical equation edited by the editing means. According to a sixth aspect of the present invention, in the document creation assistance server (1) according to the fifth aspect, the editing means (15) may edit the compound such that a looped compound, which indicates that a pre-reaction compound and a post-reaction compound are identical, is identifiable. According to a seventh aspect of the present invention, the document creation assistance server (1) according to the fifth aspect may further include a compound checking means (15) that checks the compound included in the chemical equation obtained by the chemical equation obtaining means (14) against a compound database (51) that stores compound information, in which the editing means (15) may edit the compound on the basis of a checking result from the compound checking means. According to an eighth aspect of the present invention, the document creation assistance server (1) according to any one of the fifth to seventh aspects, may further include a notebook checking means (15) that checks a description in the electronic lab notebook data related to each compound included in the chemical equation obtained by the chemical equation obtaining means (14) against a theoretical value obtained from a structural formula of each compound, in which the editing means (15) may edit the compound on the basis of a checking result from the notebook checking means. According to a ninth aspect of the present invention, the document creation assistance server (1) according to any one of the fifth to eighth aspects, may further include a selection accepting means (21) that accepts a selection of the compound included in the chemical equation output from the chemical equation outputting means (16); and an operation list outputting means (21) that outputs a list of possible operations in accordance with a nature of the compound accepted by the selection accepting means. According to a tenth aspect of the present invention, the document creation assistance server (1) according to any one of the first to ninth aspects, may further include a template storage unit (33) that stores a template (80) with a tag being embedded, in which the document generating means (17) may generate the document through a process of embedding the chemical equation obtained by the chemical equation obtaining means

(14) into the tag in the template stored in the template storage unit. According to an eleventh aspect of the present invention, in the document creation assistance server (1) according to any one of the first to tenth aspects, the document generating means (17) may convert the chemical equation into image data and generate the document containing the image data thus converted. According to a twelfth aspect of the present invention, a method of assisting with creation of a document that serves as an Example using a computer (1) includes: accepting, by the computer, identification information that identifies a final product generated through synthesis of a plurality of compounds; obtaining, by the computer, a chemical equation for generating the final product corresponding to the identification information accepted, with reference to electronic lab notebook data that electrically describes experiments related to the synthesis of the compounds; and generating, by the computer, a document including the chemical equation obtained.

Effects of the Invention

According to the present invention, a document creation assistance server and a document creation assistance method can be provided that enable efficient acquisition of information required for drafting a specification etc., and generation of a document on the basis of the information thus obtained.

BRIEF DESCRIPTION OF THE DRAWINGS

FIGS. 5A and 5B are flowcharts showing a chemical equation obtaining process in the document creation assistance server according to the present embodiment;

FIG. 6A is a drawing for illustrating an example of editing in the document creation assistance server according to the present embodiment;

FIG. 6B is a drawing for illustrating an example of editing in the document creation assistance server according to the present embodiment;

FIG. 8 is a flowchart showing a document creation process in the document creation assistance server according to the present embodiment;

FIG. 10 is a drawing showing an example of document data generated by the document creation assistance server according to the present embodiment.

PREFERRED MODE FOR CARRYING OUT THE INVENTION

Hereinafter, an embodiment of the present invention is described with reference to the drawings. The embodiment is a mere example and a technical scope of the present invention is not limited thereto.

Embodiment

<Overall Configuration of Document Creation Assistance System 100>

Figure 1:
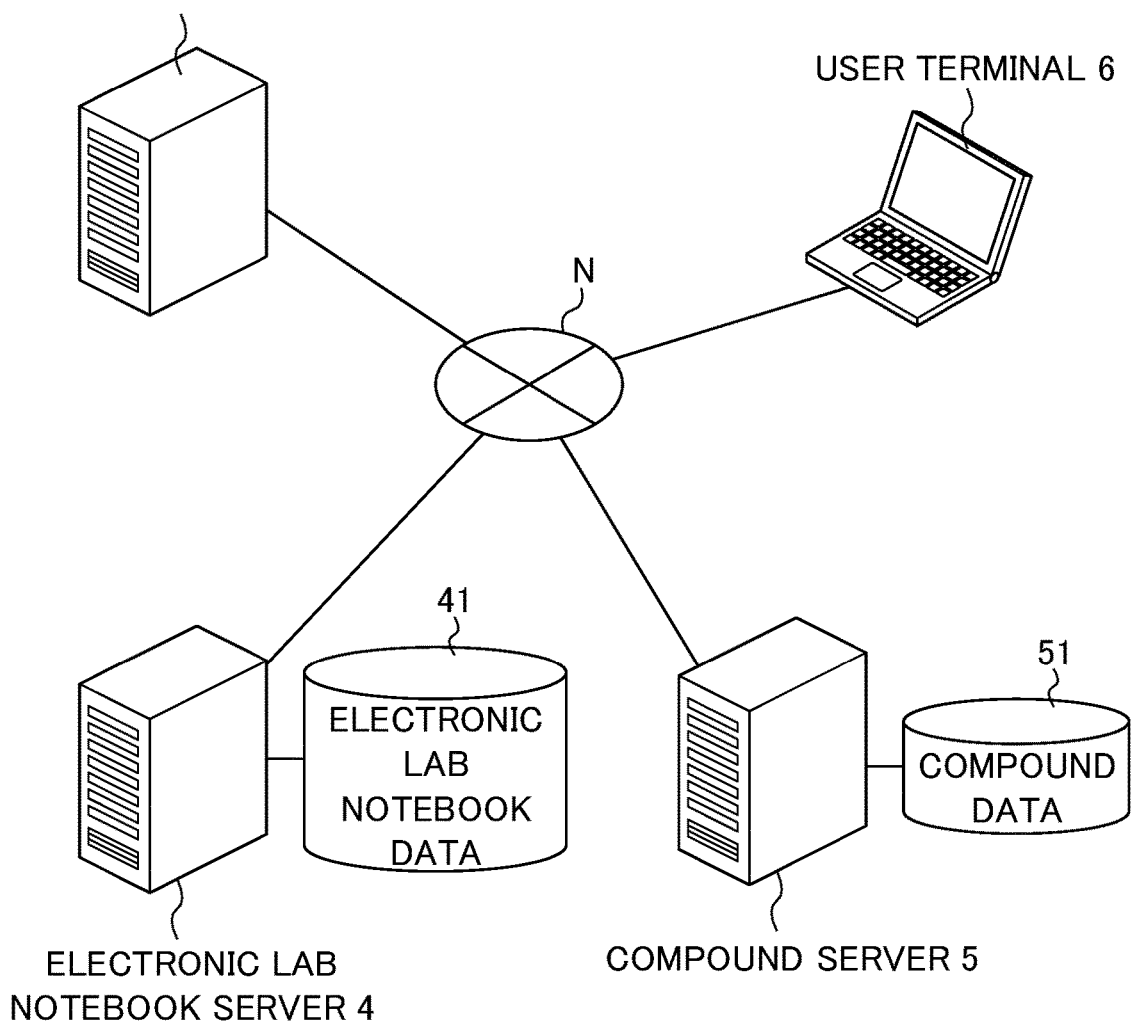
FIG. 1 is a drawing showing an overall configuration of a document creation assistance system according to the present embodiment.
Figure 2:
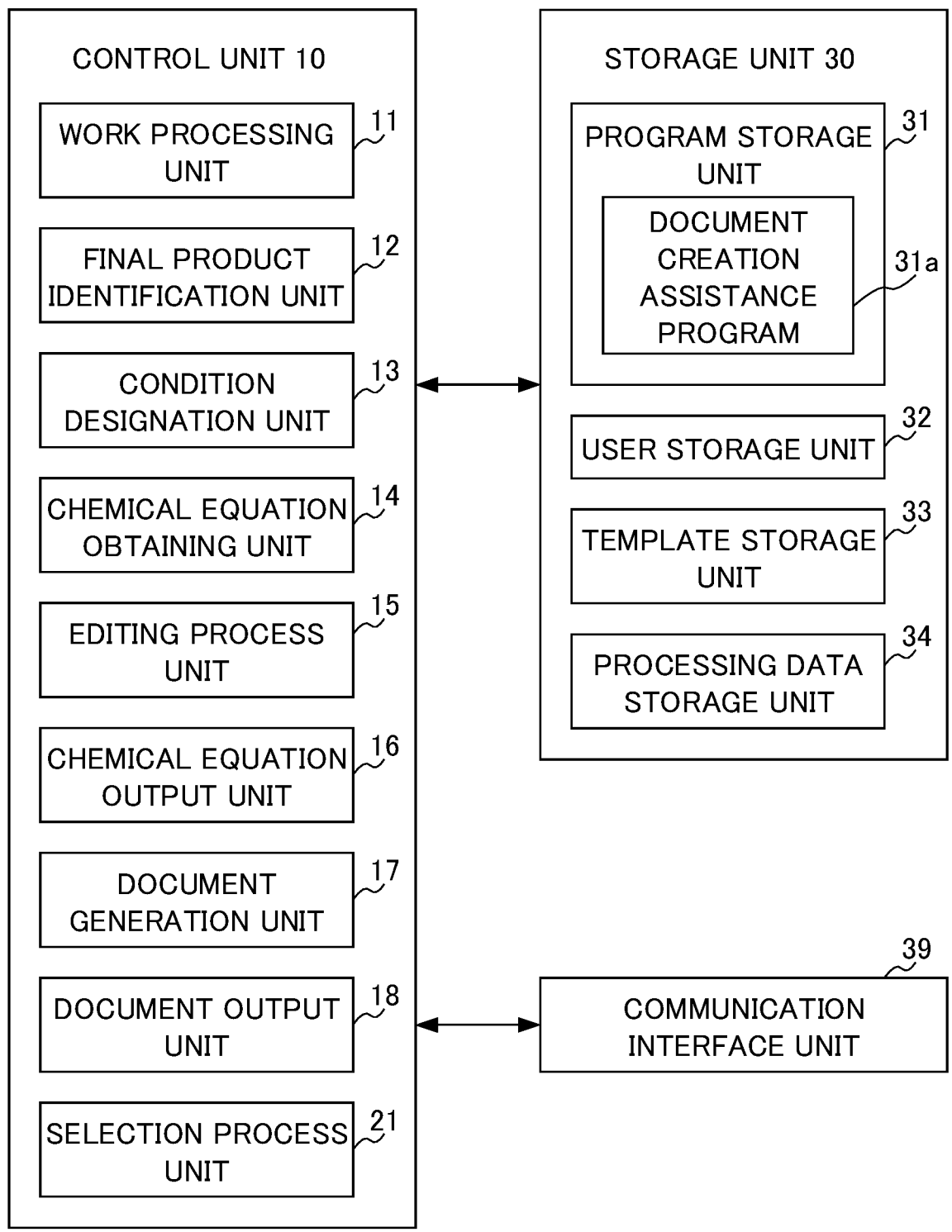
FIG. 2 is a drawing showing functional blocks of a document creation assistance server according to the present embodiment.

FIG. 1 is a drawing showing the overall configuration of the document creation assistance system 100 according to the present embodiment. FIG. 2 is a drawing showing functional blocks of a document creation assistance server 1 according to the present embodiment. The document creation assistance system 100 shown in FIG. 1 is a system for creating a document relating to generation of a compound. The document created by the document creation assistance system 100 can be used as an experimental section, and is suitable for, in particular, an Example of a patent specification and an academic paper. As used herein, the "experimental section" means a document that describes a generation procedure for a particular compound. In the experimental section, the generation procedure for the compound must be described to such a degree that the same compound can be generated with reference to the method described in the experimental section. The document creation assistance system 100 is to be used in, for example, companies that generate compounds such as pharmaceutical companies. Hereinafter, the document creation assistance system 100 is explained, generating a document for an Example to be included in a patent specification, as a document including an experimental section.

The document creation assistance system 100 includes a document creation assistance server 1, an electronic lab notebook server 4, a compound server 5, and a user terminal 6. The document creation assistance server 1, the electronic lab notebook server 4, the compound server 5, and the user terminal 6 are communicable with each other via a communication network N. The communication network N is, for example, a communication line network such as Internet. The communication network N may include a local area network (LAN) and a wide area network (WAN). In this case, in light of accessibility to the outside environment, it is preferred that the document creation assistance server 1, the electronic lab notebook server 4 and the compound server 5 are connected to each other via an in-house LAN etc., while the user terminal 6 is communicably connected to the document creation assistance server 1 by means of a VPN (Virtual Private Network) etc. Thus, the user terminal 6 can communicate with the document creation assistance server 1 from either inside or outside of the company.

<Document Creation Assistance Server 1>

The document creation assistance server 1 formats a chemical equation to be included as an Example in a specification or the like, according to a format of the specification or the like. And then the document creation assistance server 1 outputs a document including the chemical equation thus formatted to the user terminal 6. Here, the chemical equation represents generation of a compound, and can be expressed by a pre-reaction compound and a post-reaction compound (also referred to as "product") generated by using a reagent. The document creation assistance server 1 is, for example, a server. The document creation assistance server 1 may be configured with either a computer or a plurality of computers. In a case of using the plurality of computers, these computers are connected to each other via the communication network N. Alternatively, the document creation assistance server 1 may be configured as, for example, a virtual server (virtual machine) provided on a cloud.

The document creation assistance server 1 includes a control unit 10, a storage unit 30, and a communication interface unit 39. The control unit 10 is a central processing unit (CPU) that controls the document creation assistance server 1 as a whole. The control unit 10 reads and executes an operating system (OS) and an application program stored in the storage unit 30 as appropriate, to thereby cooperate with the aforementioned hardware and carry out various functions.

In the present embodiment, a mode is explained as a specific example in which the document creation assistance server 1 is realized by a computer executing a program. The program may be stored in a computer-readable non-transitory information storage medium such as: a compact disk; a flexible disk; a hard disk; a magneto-optical disk; a digital video disk; magnetic tape; ROM (Read Only Memory); EEOPROM (Electrically Erasable Programmable ROM); flash memory; semiconductor memory; and the like. The information storage medium may be distributed and sold independently from the computer.

In general, the computer loads the program stored in the non-transitory information storage medium into the RAM (Random Access Memory), which is a temporary storage device included in the storage unit 30, and then the CPU as the control unit 10 executes the program thus loaded. It is to be noted that the program may be, independently from the computer that executes the program, sold and distributed from a program distribution server or the like (not illustrated) to the computer or the like via a temporary transmission medium such as the communication network N.

Alternatively, the program may be described in a programming language designed for describing the operation level of the electronic circuit. In this case, various blueprints such as a wiring plan of the electronic circuit, a timing diagram, etc. are generated by the program described in the programming language designed for describing the operation level of the electronic circuit, and then the electronic circuit constituting the document creation assistance server 1 may be formed on the basis of the blueprints. For example, the document creation assistance server 1 may be configured on a reprogrammable hardware by the FPGA (Field-Programmable Gate Array) technology by the program described in the programming language designed for describing the operation level of the electronic circuit; and an electronic circuit for a specific purpose may be configured by the ASIC (Application-Specific Integrated Circuit) technology.

As described above, the document creation assistance server 1 is configured to execute the processes described in the present embodiment by means of the control unit 10 controlling the constitutional units mentioned below. The control unit 10 includes: a work processing unit 11; a final product identification unit 12 (identification information accepting means); a condition designation unit 13 (condition accepting means); a chemical equation obtaining unit 14 (chemical equation obtaining means); an editing process unit 15 (compound checking means, notebook checking means, editing means); a chemical equation output unit 16 (chemical equation outputting means); a document generation unit 17 (document generating means); a document output unit 18; and a selection process unit 21 (selection accepting means, operation list outputting means).

The work processing unit 11 executes a process regarding a work on the basis of a work processing request received from the user terminal 6. Hereinafter, a person who operates the user terminal 6 is referred to as "user". The user may be either a chemist who has synthesized the compound, or another person. The term "work" means a workspace to be used by the document creation assistance server 1 for creating a document including an Example. The document creation assistance server 1 uses one work for creating one document for a patent specification. In one work, a process is carried out for at least one experiment example. For example, in response to a work creation request from the user terminal 6, the work processing unit 11 creates one work and makes the work available for the user terminal 6. The work creation request includes data for creation of the work such as: a work name; language (Japanese or English); a project name; and the like, as well as designation of members to share the work. Alternatively, for example, the work processing unit 11 submits a work list showing works that are created beforehand, in response to a request from the user terminal 6. And then, in response to designation by the user terminal 6 of one work among the works in the work list, the work processing unit 11 makes the designated work available for the user terminal 6.

The final product identification unit 12 accepts identification data for the final product to be described as an Example. The term "final product" means a compound that is ultimately generated. The identification data for the final product is, for example, an identification code that identifies the final product. For example, in order to obtain the right for the final product having medicinal effects, an experiment example regarding generation of the final product must be described in the specification for patent application such that the final product can be generated by anyone having read the experiment example. The final product identification unit 12 may display the identification data for the final product from the electronic lab notebook data stored in the electronic lab notebook server 4, to thereby allow the user to select. Alternatively, the final product identification unit 12 may be configured such that the user directly inputs the identification code for the final product. In addition, the final product identification unit 12 may be configured such that a plurality of identification codes for the final products is specified.

The condition designation unit 13 designates a target range in the electronic lab notebook data. The target range is, for example, a range of chemists in the electronic lab notebook data, a range of experiment dates in the electronic lab notebook data, and the like. In addition, the condition designation unit 13 designates a condition for obtaining the electronic lab notebook data. The condition is for determining which chemical equation is to be preferentially obtained from the electronic lab notebook data. The condition designation unit 13 designates, as the condition, the most prioritized one of: yield; yielded amount; chemists; and the number of compounds included in the synthesis pathway. The condition may be either determined beforehand by the document creation assistance server 1, or designated by the user. In addition, a plurality of conditions may be designated. In this case, the user may specify, in addition to the plurality of conditions, priorities thereof.

On the basis of the identification data for the final product identified by the final product identification unit 12, the chemical equation obtaining unit 14 obtains the chemical equation of the final product within the target range in the electronic lab notebook data designated by the condition designation unit 13 according to the condition. The editing process unit 15 edits the compound included in the chemical equation obtained by the chemical equation obtaining unit 14, according to the nature of the compound. In addition, the editing process unit 15 carries out various types of checking regarding the compound included in the chemical equation obtained by the chemical equation obtaining unit 14. The editing process unit 15 may further edit the compound based on the checking result. The chemical equation output unit 16 submits the chemical equation edited by the editing process unit 15 to the user terminal 6. The user terminal 6 can thus display the edited chemical equation.

The document generation unit 17 generates a document containing the designated chemical equation. The document generation unit 17 generates a document based on a template stored in the template storage unit 33. The document thus generated is stored in the storage unit 30 of the document creation assistance server 1. The document output unit 18 submits the document generated by the document generation unit 17 to the user terminal 6.

When the user terminal 6 selects one compound for the edited chemical equation output by the chemical equation output unit 16, the selection process unit 21 accepts the selection of the compound. And then, the selection process unit 21 submits to the user terminal 6 an operation list corresponding to the compound accepted. The operation list corresponds to the nature of the compound. For example, in a case in which the compound accepted is a looped compound which indicates that a pre-reaction compound and a post-reaction compound are identical, the operation list includes options for resolving the loop and options for dividing a lot.

The storage unit 30 is a storage area in a hard disk, semiconductor memory, etc. for storing programs, data, and the like required for the control unit 10 to execute various processes. The storage unit 30 includes a program storage unit 31, a user storage unit 32, a template storage unit 33 and a processing data storage unit 34. The program storage unit 31 is a storage area for storing various programs. The program storage unit 31 stores a document creation assistance program 31*a*. The document creation assistance program 31*a* executes the aforementioned functions of the control unit 10.

The user storage unit 32 is for management of the user who uses the user terminal 6. The user storage unit 32 stores, for example, a user ID, a user name, etc. of the user who uses the document creation assistance system 100, in association with each other. The template storage unit 33 is a storage area for storing templates used for document creation. The template storage unit 33 stores templates at least in Japanese and English. The processing data storage unit 34 is a storage area for storing data used for each work. The communication interface unit 39 allows communication between the electronic lab notebook server 4, the compound server 5, and the user terminal 6.

<Electronic Lab Notebook Server 4>

The electronic lab notebook server 4 is a server that executes processes regarding the electronic lab notebook data. The electronic lab notebook server 4 is provided with a lab notebook data storage unit 41 that stores the electronic lab notebook data. The electronic lab notebook server 4 is further provided with: a control unit that executes a process of generating electronic lab notebook data, and the like; a communication interface unit for communicating with the document creation assistance server 1; and the like (not illustrated). The electronic lab notebook server 4 may be a server available from various companies.

<Compound Server 5>

The compound server 5 manages the nature of the compound. The compound server 5 is provided with a compound data storage unit (compound database) 51 that stores compound data. The compound data storage unit 51 stores compound data. The compound data includes a compound name, a compound number that identifies the compound, and the like. The compound data stored in the compound data storage unit 51 has, for example, a flag that indicates that the compound is a source material. As used herein, the "source material" means a starting material which is commercially available and does not need synthesis. The compound server 5 is further provided with a control unit, a communication interface unit, and the like (not illustrated).

<User Terminal 6>

The user terminal 6 is a terminal used by each user. The user terminal 6 communicates with the document creation assistance server 1 and provides an instruction of a process for document creation to the document creation assistance server 1. The user terminal 6 is, for example, a personal computer (PC). The user terminal 6 is provided with a control unit, a storage unit, a communication interface unit, a display unit, an input unit, and the like (not illustrated).

It is to be noted that the term "computer" means an information processing device provided with a control unit, a storage device, and the like. The document creation assistance server 1, the electronic lab notebook server 4, the compound server 5 and the user terminal 6 are information processing devices provided with a control unit, a storage device, and the like, and therefore fall under the concept of "computer".

<Description of Process>

Figure 3:
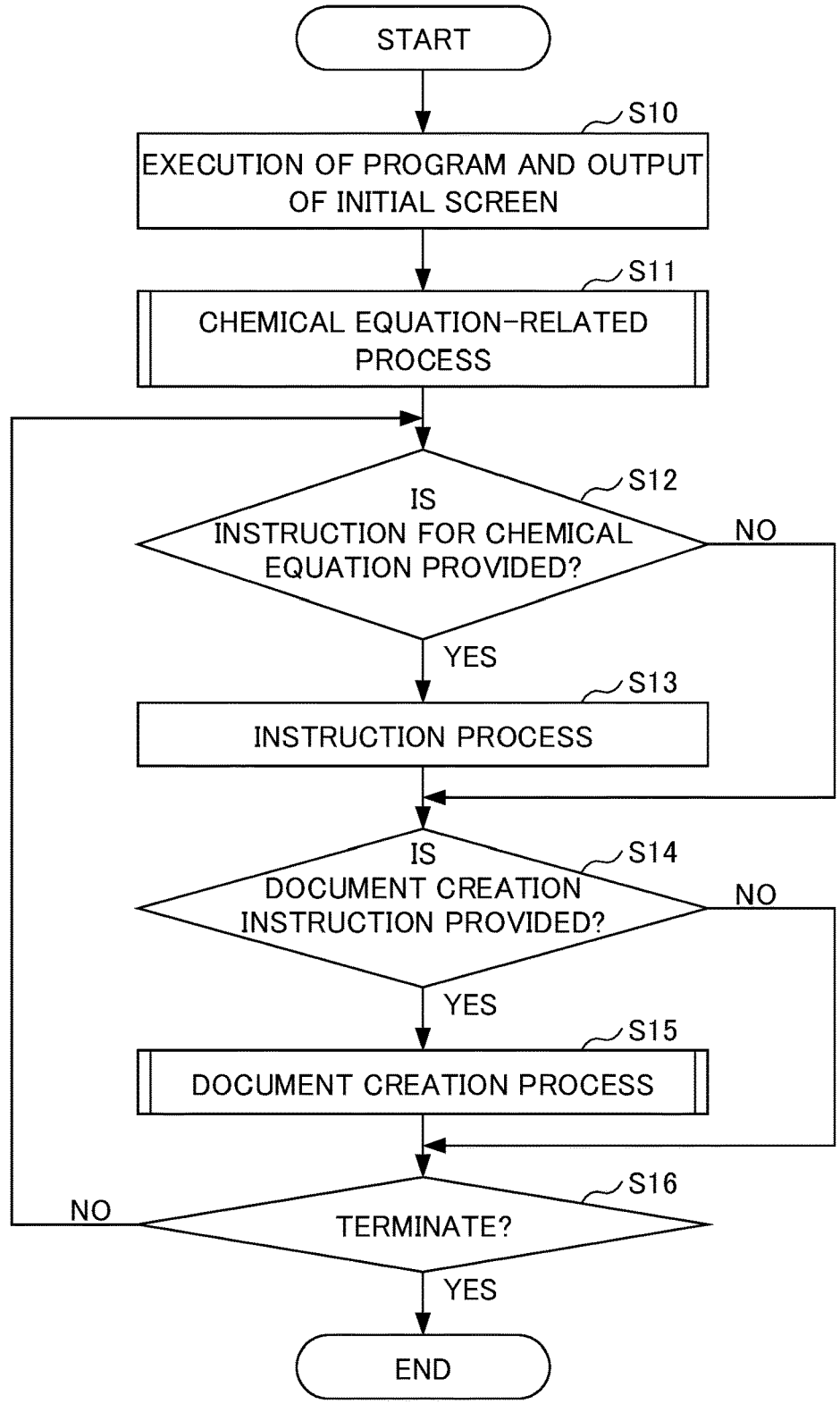
FIG. 3 is a flowchart showing a document creation assistance process in the document creation assistance server according to the present embodiment.
Figure 4:
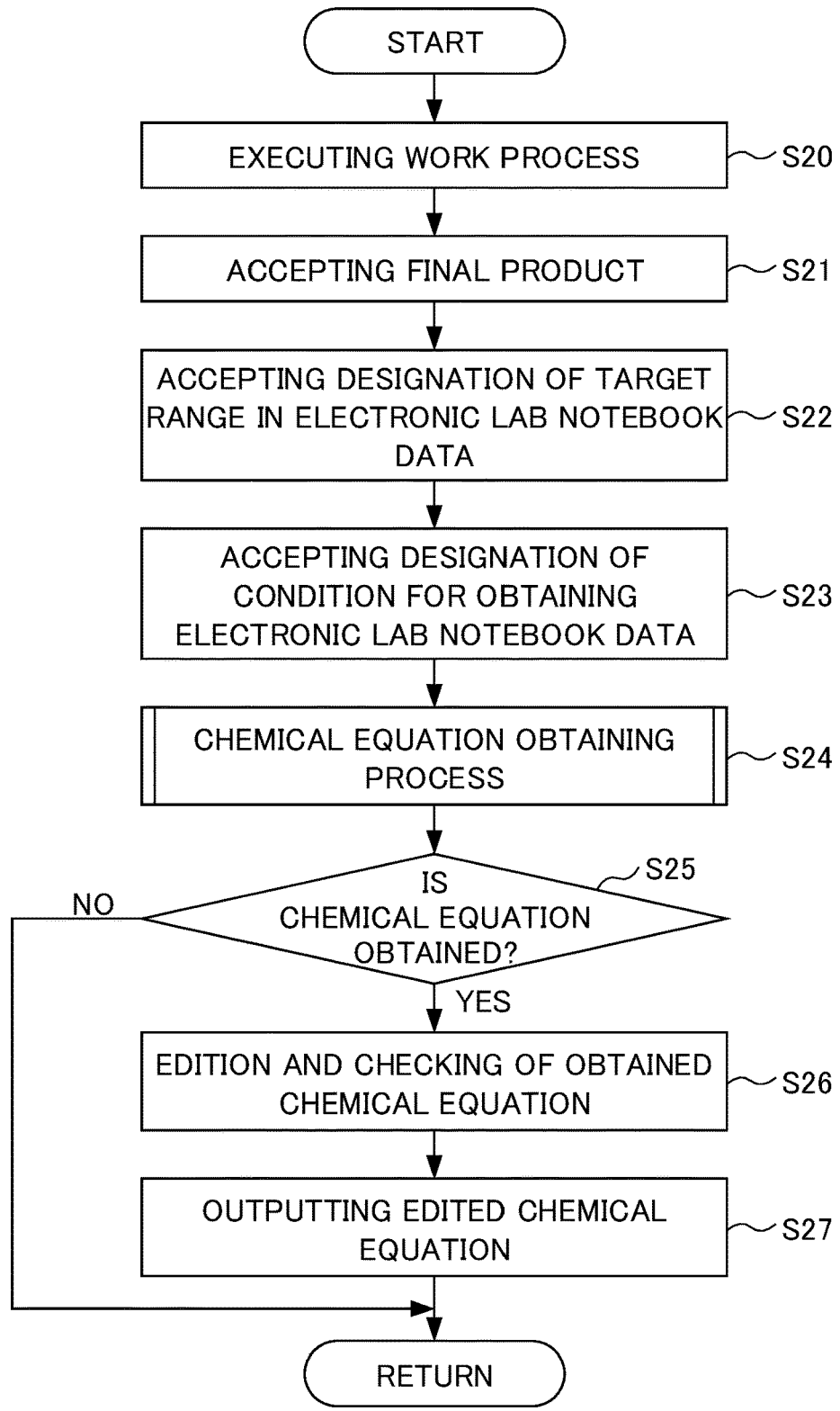
FIG. 4 is a flowchart showing a chemical equation-related process in the document creation assistance server according to the present embodiment.
Figure 6C:
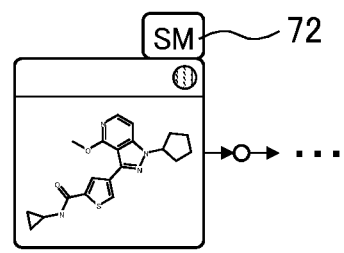
FIG. 6C is a drawing for illustrating an example of editing in the document creation assistance server according to the present embodiment.
Figure 6D:
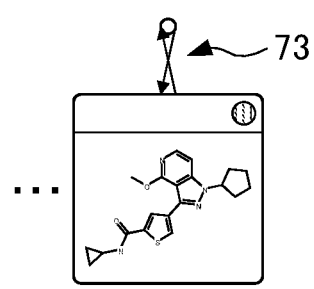
FIG. 6D is a drawing for illustrating an example of editing in the document creation assistance server according to the present embodiment.
Figure 7A:
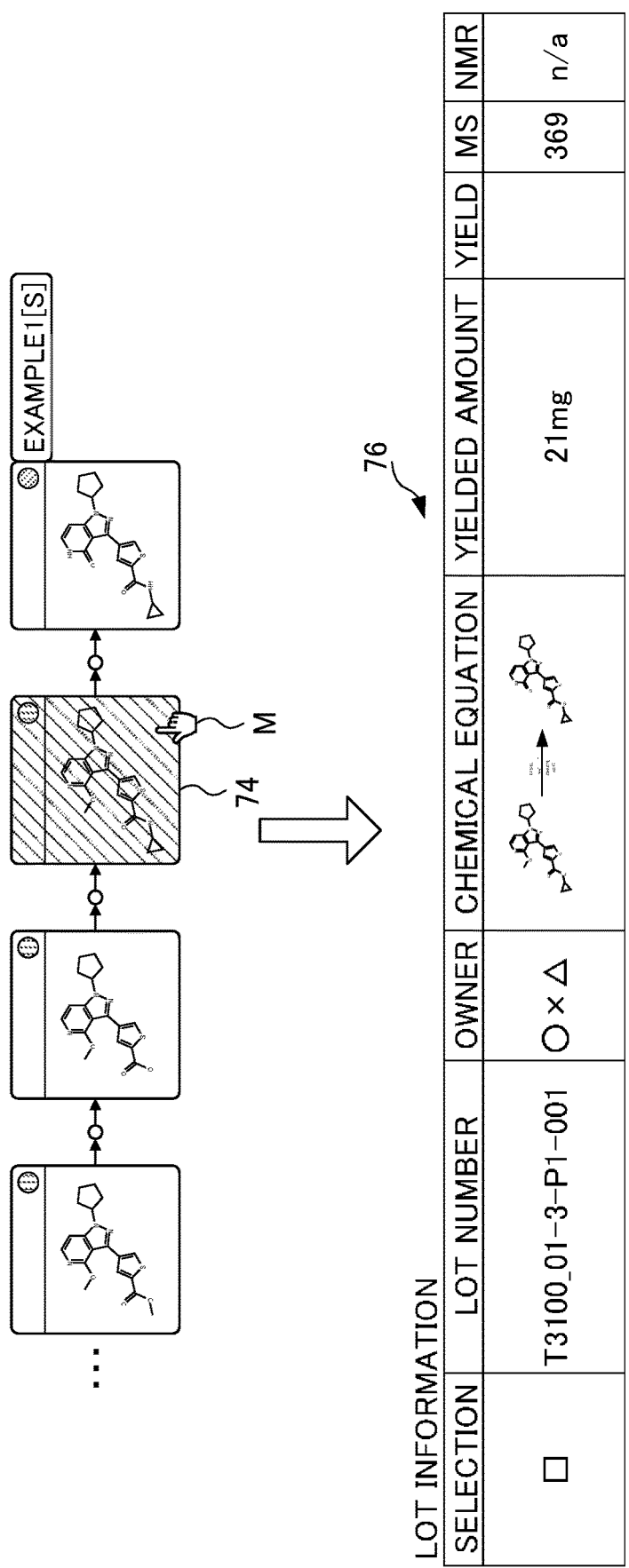
FIG. 7A is a drawing for illustrating a specific example of an instruction regarding the chemical equation in the document creation assistance server according to the present embodiment.
Figure 7B:
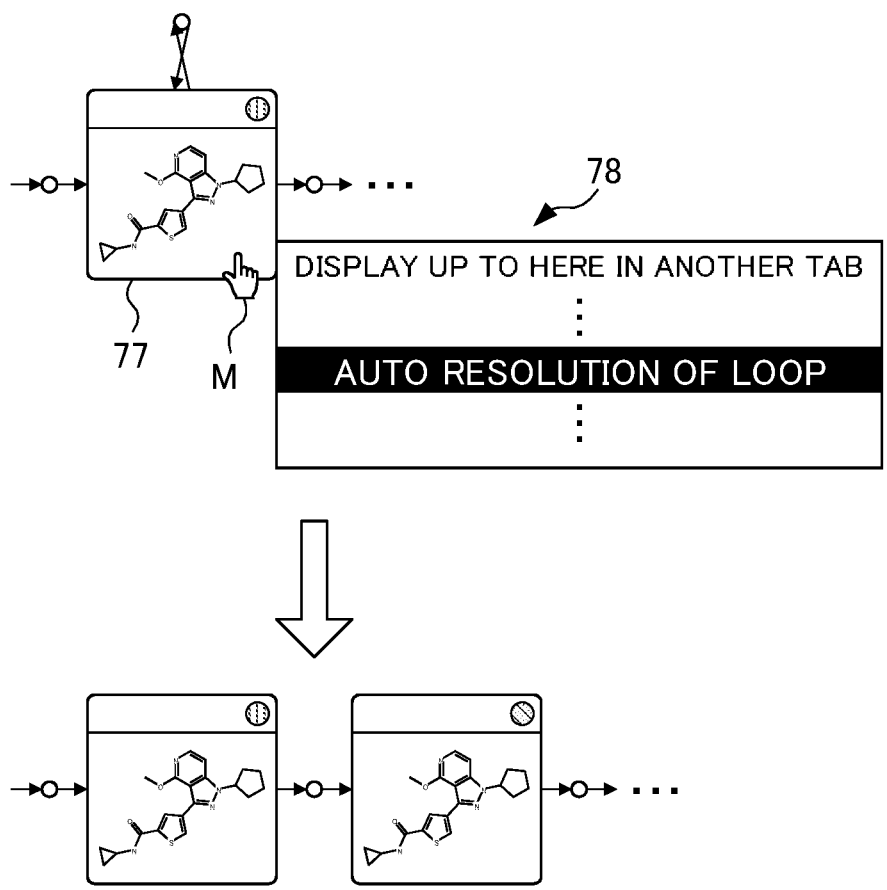
FIG. 7B is a drawing for illustrating a specific example of an instruction regarding the chemical equation in the document creation assistance server according to the present embodiment.
Figure 9:
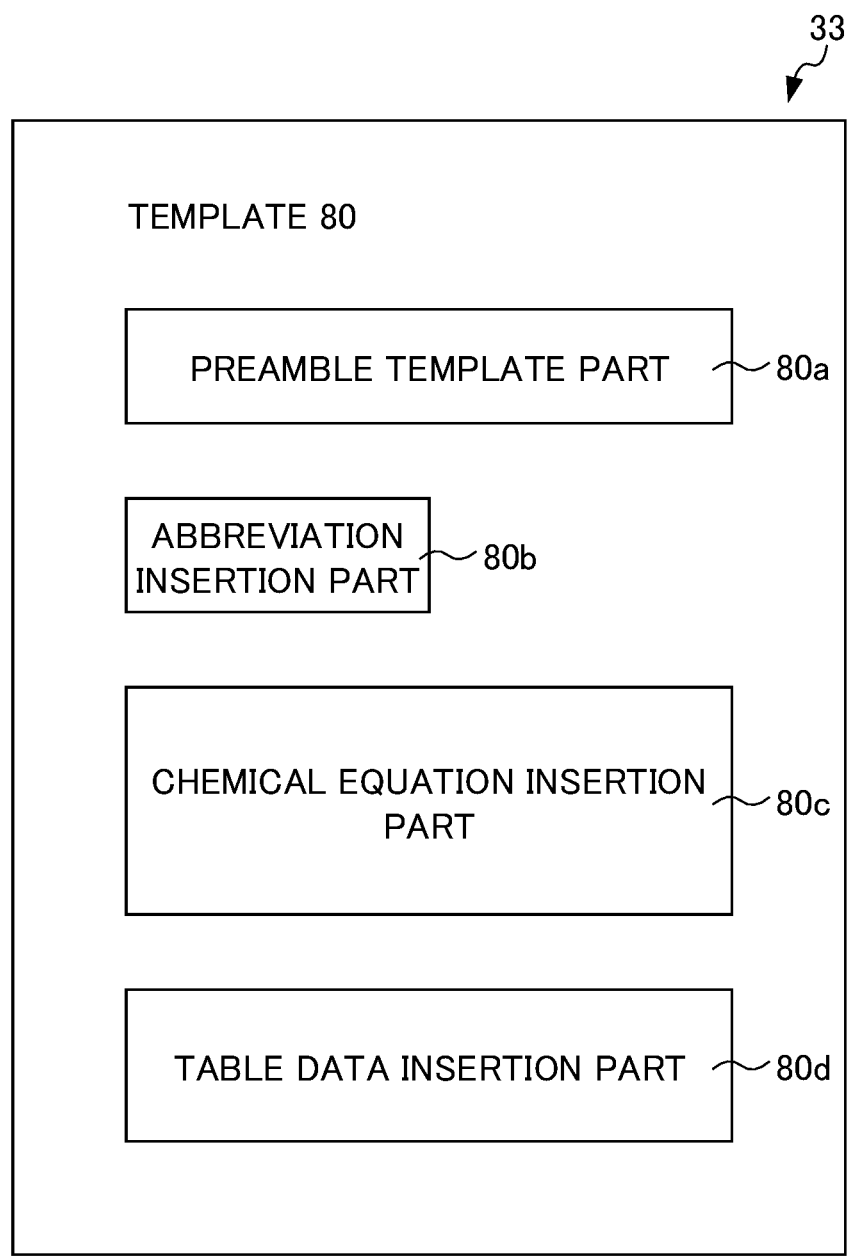
FIG. 9 is a drawing showing an example of a template stored in a template storage unit of the document creation assistance server according to the present embodiment.

Hereinafter, a document creation assistance process by the document creation assistance system 100 is described. FIG. 3 is a flowchart showing the document creation assistance process in the document creation assistance server 1 according to the present embodiment. FIG. 4 is a flowchart showing a chemical equation-related process in the document creation assistance server 1 according to the present embodiment. FIGS. 5A and 5B are flowcharts showing a chemical equation obtaining process in the document creation assistance server 1 according to the present embodiment. FIGS. 6A to 6D are drawings for illustrating an example of editing in the document creation assistance server 1 according to the present embodiment. FIGS. 7A and 7B are drawings for illustrating a specific example of an instruction regarding the chemical equation in the document creation assistance server 1 according to the present embodiment. FIG. 8 is a flowchart showing the document creation process in the document creation assistance server 1 according to the present embodiment. FIG. 9 is a drawing showing an example of a template 80 stored in the template storage unit 33 of the document creation assistance server 1 according to the present embodiment. FIG. 10 is a drawing showing an example of document data 82 generated by the document creation assistance server 1 according to the present embodiment.

First, when the user selects an icon (not illustrated) for the document creation assistance displayed on the user terminal 6, the user terminal 6 starts communication with the document creation assistance server 1. Then, in step (hereinafter merely referred to as "S") 10 in FIG. 3, the control unit 10 of the document creation assistance server 1 accepts a request from the user terminal 6 and executes the document creation assistance program 31a. The control unit 10 executes an authentication process with the user terminal 6 for checking the user, and then outputs an initial screen (not illustrated) to the user terminal 6. The initial screen is a menu screen including a list of various processes. The user can select various processes from the list displayed on the initial screen.

If the user selects a work process, in S11, the control unit 10 executes the chemical equation-related process. Hereinafter, the chemical equation-related process is explained with reference to FIG. 4. In S20 in FIG. 4, the control unit 10 (work processing unit 11) opens the work on the basis of a work processing request received from the user terminal 6. On the basis of the work processing request, the control unit 10 makes a newly-created work or a designated work available. In S21, the control unit 10 (final product identification unit 12) accepts identification data for the final product to be described as an Example. The control unit 10 accepts, for example, an identification code of the final product from the user terminal 6. Alternatively, for example, an experiment example number in the electronic lab notebook data may be provided as the identification data. As described above, the control unit 10 can accept one of references that can identify various final products. Here, the control unit 10 may register, along with the identification data for the final product, importance of the final product. In this case, the control unit 10 accepts the identification data for the final product including importance from the user terminal 6, and then stores the identification code and the importance of the final product in association with each other. It is to be noted that the importance corresponds to, for example, the number of items to be checked in a checking process described later.

In S22, the control unit 10 (condition designation unit 13) accepts designation of a target range in the electronic lab notebook data from the user terminal 6. The target range may be designated by, for example, a target period, a chemist name, a project name, a notebook number, and the like. The target range in the electronic lab notebook data needs to be specified, because a search for required information in the electronic lab notebook data, which is enormous, may be time- and resource-consuming.

In S23, the control unit 10 (condition designation unit 13) accepts, from the user terminal 6, designation of a condition for obtaining the electronic lab notebook data. The condition is, for example: preference for yielded amount; preference for yield; specified chemist; preference for the number of compounds included in the synthesis pathway; or the like. In a case in which there is a plurality of synthesis pathways for the final product, the condition is used for specifying priorities of the pathways. It is to be noted that a sequence of the processes of S21 to S23 is arbitrary.

In S24, the control unit 10 (chemical equation obtaining unit 14) executes the chemical equation obtaining process. Hereinafter, the chemical equation obtaining process is explained with reference to FIGS. 5A and 5B. In S40 in FIG. 5A, the control unit 10 extracts from the electronic lab notebook server 4 the electronic lab notebook data within the target range in the electronic lab notebook data, and stores in the processing data storage unit 34. Here, the processing data storage unit 34 only stores the electronic lab notebook data within the target range in the electronic lab notebook data stored in the lab notebook data storage unit of the electronic lab notebook server 4. By using the electronic lab notebook data stored in the processing data storage unit 34 in the subsequent processes, these processes can be executed without the need for communication with the electronic lab notebook server 4 in an environment with the suppressed data volume. As a result, the document creation assistance server 1 is capable of faster execution of the processes than in the case of executing the processes while communicating with the electronic lab notebook server 4.

In S41, the control unit 10 searches, in the electronic lab notebook data stored in the processing data storage unit 34, for a chemical equation containing the final product corresponding to the accepted identification code as the synthesized compound. It is to be noted that the control unit 10 may also output a result of the search for the chemical equation containing the final product corresponding to the accepted identification code to a search result screen (not illustrated) displayed on the user terminal 6. In this way, the user may select conditions for a chemical equation to be ultimately obtained, on the basis of the search result screen output to the user terminal 6. In the following description, the chemical equation is obtained according to the condition designated by internal process, without the user's selection.

In S42, the control unit 10 determines if at least one chemical equation could be obtained as the search result. In the case in which at least one chemical equation is obtained (S42: YES), the control unit 10 advances the process to S44. On the other hand, in the case in which at least one chemical equation is not obtained (S42: NO), the control unit 10 advances the process to S43. In S43, the control unit 10 informs the user terminal 6 that no chemical equation is obtained and there is no relevant result, and then terminates the present process and moves onto the process of FIG. 4. Meanwhile, in S44, the control unit 10 identifies one chemical equation from the chemical equations obtained according to the condition. And then, the control unit 10 stores the identified chemical equation in the processing data storage unit 34.

In S45, the control unit 10 determines if a pre-reaction compound in the identified chemical equation is the source material, with reference to the compound data storage unit 51 in the compound server 5. In the case in which the pre-reaction compound is the source material (S45: YES), the control unit 10 terminates the present process and moves onto the process of FIG. 4. On the other hand, in the case in which the pre-reaction compound is not the source material (S45: NO), the control unit 10 advances the process to S46 in FIG. 5B. In S46 in FIG. 5B, the control unit 10 determines if the pre-reaction compound in the identified chemical equation is the starting material. In the case in which the pre-reaction compound is the starting material (S46: YES), the control unit 10 terminates the present process and moves onto the process of FIG. 4. On the other hand, in the case in which the pre-reaction compound is not the starting material (S46: NO), the control unit 10 advances the process to S47. As used herein, the "starting material" means a compound which is not the source material and serves as a branch point to another chemical equation. In S47, the control unit 10 uses the electronic lab notebook data stored in the processing data storage unit 34 to search a chemical equation in which a post-reaction compound is identical to the pre-reaction compound in the identified chemical equation. In S48, the control unit 10 determines if at least one chemical equation could be obtained as the search result. In the case in which at least one chemical equation could be obtained (S48: YES), the control unit 10 advances the process to S44 in FIG. 5A and repeats the process. On the other hand, in the case in which at least one chemical equation is not obtained (S48: NO), the control unit 10 terminates the present process and moves onto the process of FIG. 4.

Again in FIG. 4, in S25, the control unit 10 determines if a chemical equation could be obtained in the chemical equation obtaining process. In the case in which a chemical equation could be obtained (S25: YES), the control unit 10 advances the process to S26. On the other hand, in the case in which a chemical equation could not be obtained (S25: NO), the control unit 10 terminates the present process and moves onto the process of FIG. 3. The case in which a chemical equation could not be obtained means, for example, a case in which the electronic lab notebook data does not contain a chemical equation relating to the identified final product. In S26, the control unit 10 (editing process unit 15) edits and checks the chemical equation obtained by the chemical equation obtaining process.

Hereinafter, the editing of the chemical equation is explained with reference to specific examples shown in FIGS. 6A to 6D. A chemical equation 70 shown in FIG. 6A is the chemical equation obtained by the chemical equation obtaining process, with the final product 70a on the rightmost side and a plurality of compounds being arranged in the order of synthesis connected with arrows. The control unit 10 determines if each compound contained in the obtained chemical equation has a corresponding compound stored in the compound data storage unit 51 in the compound server 5. In a case in which the compound has a corresponding compound stored in the compound data storage unit 51, the control unit 10 displays a mark 71a, which indicates presence, at an upper right corner of the compound as shown in FIG. 6B. On the other hand, in a case in which the compound does not have a corresponding compound stored in the compound data storage unit 51, the control unit 10 displays a mark 71b, which indicates absence, at the upper right corner of the compound as shown in FIG. 6B. The case in which the compound does not have a corresponding compound stored in the compound data storage unit 51 is, for example: a case in which the compound is not registered in the compound data storage unit 51; a case in which a name, etc. of the compound is different between the compound data storage unit 51 and the electronic lab notebook data; and the like. In addition, a case in which compounds of the same structure having different lot numbers is also the case in which the compound does not have a corresponding compound stored in the compound data storage unit 51.

The control unit 10 may check the content regarding each compound contained in the obtained chemical equation in the electronic lab notebook data, against a compound structural formula corresponding to each compound in the electronic lab notebook. More specifically, the control unit checks correctness of NMR data (hydrogen number) and MS data (molecular weight value) extracted from the electronic lab notebook data against the (structural formula information of) product of the chemical equation. For example, in regard to MS, a value within a range of ±0.5 of the exact mass value obtained from the structural formula+1 is considered to be a normal value. In addition, for example, in regard to NMR data format, with the format (A) below, the control unit 10 obtains a sum of all values preceding H and checks whether the sum is equal to the number of hydrogens in the structural formula (including implicit hydrogen).

(A) 1H NMR (300 MHz, DMSO-d6) δ 0.45-0.79 (4H, m), 1.70 (6H, s), 2.20 (3H, d, J=2.3 Hz), 2.76-2.94 (1H, m), 3.90 (2H, d, J=6.8 Hz), 5.01 (1H, t, J=6.4 Hz), 7.26 (1H, dd, J=7.0, 1.9 Hz), 7.49-7.75 (2H, m), 7.93 (1H, d, J=1.9 Hz), 8.49 (1H, d, J=4.1 Hz), 11.19 (1H, brs). During this checking, a difference may be absorbed by inputting a correction value. In addition, as a result of the checking, in the case of being incorrect, the control unit 10 may display at the upper right corner of the compound a mark indicating that the checking result of the electronic lab notebook data was incorrect.

Furthermore, for the compound which is a source material or a starting material, the control unit 10 displays a mark 72, which indicates a source material or a starting material, in a display area of the compound as shown in FIG. 6C. Moreover, in a case of the compound in which a pre-reaction compound and a post-reaction compound are identical, i.e., a looped compound, the control unit 10 displays a loop mark 73 in the display area of the compound as shown in FIG. 6D. The compound in which a pre-reaction compound and a post-reaction compound are identical is exemplified by a compound during purification process (for example, column chromatography, recrystallization, and the like).

As a checking process for the chemical equation, the control unit 10 carries out checking according to the importance of the final product. For example, the control unit 10 carries out checking with many check items for the chemical equation of which final product is high in importance, while the control unit 10 carries out checking with a few check items for the chemical equation of which final product is low in importance. In addition, the control unit 10 may edit the checking result into a chemical equation. The editing may be, for example, changing of the color of compound name, output of a check result as a pop-up message, and the like.

Again in FIG. 4, in S27, the control unit 10 (chemical equation output unit 16) submits the edited chemical equation to the user terminal 6. The user terminal 6 can thus display the edited chemical equation in a chemical equation display area (not illustrated) of the work. The user terminal 6 can then execute various processes using the edited chemical equation thus displayed. And then, the control unit 10 terminates the present process and moves onto the process of FIG. 3.

Again in FIG. 3, in S12, the control unit 10 determines if a selection instruction was provided by selecting a chemical equation. In the case in which the selection instruction was provided (S12: YES), the control unit 10 advances the process to S13. On the other hand, in the case in which the selection instruction was not provided (S12: NO), the control unit 10 advances the process to S14. In S13, the control unit 10 (selection process unit 21) executes an instruction process.

Hereinafter, the process in response to the instruction is explained with reference to specific examples shown in FIGS. 7A and 7B. For example, supposing that, in response to the edited chemical equation being output to the user terminal 6, the user operates a selection mark M in FIG. 7A from the user terminal 6 to select one compound display area 74. The control unit 10 then accepts from the user terminal 6 the selection of the compound at the compound display area 74 indicated by the selection mark M. And then, the control unit 10 obtains and then outputs detailed data 76 of the compound at the compound display area 74 from the electronic lab notebook data stored in the processing data storage unit 34. The detailed data 76 includes various data such as the chemical equation, a lot number for identifying the chemical equation and a yielded amount. The chemical equation includes a pre-reaction compound, a post-reaction compound, and a reagent. In a case in which MS data or NMR data is determined to be incorrect as a result of the checking process using the electronic lab notebook data described above, the control unit 10 may notify an error value by displaying color corresponding to the degree of incorrectness in a MS field or an NMR field in the detailed data 76.

Alternatively, supposing that, for example, in response to the edited chemical equation being output to the user terminal 6, the user selects from the user terminal 6 a compound indicating the loop as illustrated by the selection mark M in FIG. 7B. The control unit 10 then accepts from the user terminal 6 the selection of the compound indicated by the selection mark M. And then, the control unit 10 generates and submits to the user terminal 6 the operation list 78 corresponding to the compound accepted. In a case in which the selection of one option from the operation list 78 is accepted, the control unit 10 executes a process corresponding to the option accepted. For example, in a case in which the process corresponding to the option accepted is a process for resolving the loop, the control unit 10 modifies the chemical equation so as to resolve the loop, as shown in FIG. 7B. It is to be noted that these processes update the data stored in the processing data storage unit 34 of the document creation assistance server 1, but not the original electronic lab notebook data.

Again in FIG. 3, in S14, the control unit 10 determines if a document creation instruction was provided. In the case in which the document creation instruction was provided (S14: YES), the control unit 10 advances the process to S15. On the other hand, in the case in which the document creation instruction was not provided (S14: NO), the control unit 10 advances the process to S16.

In S15, the control unit 10 (document generation unit 17, document output unit 18) executes the document creation process. Hereinafter, the document creation process is explained with reference to FIG. 8. In S60 in FIG. 8, the control unit 10 (document generation unit 17) extracts a template from the template storage unit 33. Here, the control unit 10 extracts a template in the language selected upon creation of the work. For example, in a case in which the language selected upon creation of the work is English, a template in English is extracted; and in a case in which the language selected upon creation of the work is Japanese, a template in Japanese is extracted. It is to be noted that the type of template may be selected by the user prior to the start of the document creation process.

FIG. 9 shows an example of the template 80. The template 80 has a preamble template part 80*a*, an abbreviation insertion part 80*b*, a chemical equation insertion part 80*c*, and a table data insertion part 80*d*. The preamble template part 80*a* is a part in which the experiment conditions described in the electronic lab notebook data are to be embedded into a template text defined and stored in advance, used for drafting a preamble of an Example. The abbreviation insertion part 80*b* is a part in which an explanation of abbreviation is to be embedded. The chemical equation insertion part 80*c* is a part in which a chemical equation is to be embedded. The table data insertion part 80*d* is a part in which a compound of an experiment example is to be embedded in a form of table. The template 80 has tags being embedded. In the process described below, a content of the electronic lab notebook data is embedded into the tag in the template 80.

Again in FIG. 8, in S61, the control unit 10 (document generation unit 17) embeds the electronic lab notebook data into the extracted template 80. First, the control unit 10 executes a process of embedding experiment conditions described in the electronic lab notebook data into the preamble template part 80*a*. The electronic lab notebook data used for the process is the data stored in the processing data storage unit 34. Next, the control unit 10 embeds an explanation of abbreviation into the abbreviation insertion part 80*b*. The control unit 10 outputs an abbreviation on the template to the abbreviation insertion part 80*b*, and in a case in which the predetermined structural formula is present in the electronic lab notebook data, outputs the abbreviation to the abbreviation insertion part 80*b*. It is to be noted that the control unit 10 ultimately converts the structural formula thus output into an abbreviation.

In S62, the control unit 10 (document generation unit 17) generates image data of the chemical equation and embeds into the chemical equation insertion part 80*c* of the template 80. The control unit 10 extracts the relevant chemical equation from the electronic lab notebook data. And then, the control unit 10 generates image data of the chemical equation thus extracted. The chemical equation in the electronic lab notebook data is in a format editable by a drawing software for chemical structural formula and therefore large in volume. The volume of the chemical equation may be reduced by generating the image data. The control unit 10 then outputs the image data of the chemical equation to the chemical equation insertion part 80*c* together with the explanation of the chemical equation described in the electronic lab notebook data. In S63, the control unit 10 (document generation unit 17) generates and embeds table data into the table data insertion part 80*d* of the template 80. The control unit 10 generates the table data from a name and a structural formula of the final product, and the like. The control unit 10 then outputs the table data thus generated to the table data insertion part 80*d*. It is to be noted that a sequence of the processes of S61 to S63 is arbitrary.

In S64, the control unit 10 (document output unit 18) outputs to the user terminal 6 the document embedded into the template 80. FIG. 10 shows an example of the document data 82 generated by using the template 80 shown in FIG. 9. Here, the data 82*a* corresponds to the preamble template part 80*a* in FIG. 9, while the data 82*b* corresponds to the abbreviation insertion part 80*b* in FIG. 9. In the same way, the data 82*c* corresponds to the chemical equation insertion part 80*c* in FIG. 9, while the data 82*d* corresponds to the table data insertion part 80*d* in FIG. 9. Again in FIG. 8, the control unit 10 terminates the present process and moves onto the process of FIG. 3.

Again in FIG. 3, in S16, the control unit 10 determines if the document creation assistance program 31*a* is to be terminated. In response to an instruction of terminating the program, the control unit 10 determines that the document creation assistance program 31*a* is to be terminated. In a case in which the document creation assistance program 31*a* is to be terminated (S16: YES), the control unit 10 terminates the present process. On the other hand, in a case in which the document creation assistance program 31*a* is not to be terminated (S16: NO), the control unit 10 advances the process to S12. When creation of a document for another Example is necessary, the process may go back to S11 on the same work, or another work may be opened to start a process.

According to the document creation assistance server 1 of the present embodiment described above, the following effects are produced.

(1) A final product, which is a compound for which a document is to be generated, is accepted and the document is generated by obtaining from the electronic lab notebook data a chemical equation of a compound for generating the final product. As a result, document creation can be automated by obtaining information required for drafting a specification etc. from the electronic lab notebook data and generating a document on the basis of the obtained information.

(2) Information required for an Example of a patent specification and an academic paper can be generated as a document, since chemical equations included in the synthesis pathway between a source material and the final product.

(3) A chemical equation can be obtained according to desired condition specified by the user, since a condition, which is at least one of: yield; yielded amount; chemist; and the number of compounds included in the synthesis pathway, is accepted and a chemical equation is obtained according to the condition.

(4) A compound can be edited to be easily understood by the user, since the compound included in the chemical equation obtained is edited to correspond to a nature of the compound and a chemical equation including the edited compound is output.

(5) The case in which a pre-reaction compound and a post-reaction compound are identical can be clearly indicated, since the chemical equation is presented to show the loop state.

(6) The compound can be accurately described in the document, since it is determined if the compound is stored in the compound server 5 and the compound is edited according to the determination result, allowing verification of the name, etc. of the compound.

(7) The user can easily edit since, upon selection of a compound, an operation list corresponding to the compound is output.

(8) Since the chemical equation is converted into image data upon document creation, the data volume can be suppressed, and the chemical equation can be handled as image data during editing of the document, facilitating the editing operation.

(9) Omission of required items can be prevented and consistent documents can be generated, since a document is generated by using a template defined in advance.

The embodiment of the present invention has been described above; however, the present invention is not in any way limited to the embodiments. The effects described in the embodiment are merely desirable effects produced by the present invention, and the effect of the present invention is not in any way limited to those listed in the embodiment. It is to be noted that the embodiment descried above and the modifications described below can be combined as appropriate; however, detailed description is omitted herein.

Modifications (1) In the present embodiment, the chemical equation obtaining process in which the chemical equation satisfying the condition is selected one by one retrospectively from the final product has been described; however, the present invention is not limited thereto. Alternatively, for example, the entire synthesis pathway may be first generated from the final product and then the chemical equations satisfying the condition may be selected. For obtaining a case of the smallest number of compounds included in the synthesis pathway, this method is easier.

(2) In the present embodiment, generation of a document in Japanese has been described; however, the present invention is not limited thereto. The present invention may be employed for generation of multilingual documents such as a document in English.

(3) In the present embodiment, the checking of the electronic lab notebook data by using the compound data stored in the compound data storage unit has been described; however, the present invention is not limited thereto. Alternatively, for example, a database can be accessed through network connection for checking various types of electronic lab notebook data such as the reagent data. The check result can also be displayed on a screen or output to a document file.

(4) The chemical equation presented to show the loop state in the case in which a pre-reaction compound and a post-reaction compound are identical has been described; however, the present invention is not limited thereto. The loop state may also be shown in arbitrary segments as needed.

EXPLANATION OF REFERENCE NUMERALS

1 Document creation assistance server 1
4 Electronic lab notebook server
5 Compound server
6 User terminal
10 Control unit
12 Final product identification unit
13 Condition designation unit
14 Chemical equation obtaining unit
15 Editing process unit
16 Chemical equation output unit
17 Document generation unit
21 Selection process unit
30 Storage unit
31*a* Document creation assistance program
33 Template storage unit
34 Processing data storage unit
100 Document creation assistance system

The invention claimed is:

1. A document creation assistance server for assisting with creation of a document that serves as an Example, comprising:
    an identification information accepting means that accepts identification information that identifies a final product generated through synthesis of a plurality of compounds;
    a chemical equation obtaining means that obtains a chemical equation for generating the final product corresponding to the identification information accepted by the identification information accepting means, with reference to electronic lab notebook data that electrically describes experiments related to the synthesis of the compounds; and
    a document generating means that generates a document containing the chemical equation obtained by the chemical equation obtaining means.

2. The document creation assistance server according to claim 1, wherein
    the chemical equation obtaining means obtains the chemical equation included in a synthesis pathway between a source material and the final product.

3. The document creation assistance server according to claim 1, further comprising
    a condition accepting means that accepts a condition for obtaining the chemical equation,
    wherein the chemical equation obtaining means obtains the chemical equation according to the condition.

4. The document creation assistance server according to claim 3, wherein
    the condition relates to at least one of: yield; yielded amount; chemist; and the number of compounds included in the synthesis pathway.

5. The document creation assistance server according to claim 1, further comprising:
- an editing means that edits the compound included in the chemical equation obtained by the chemical equation obtaining means, so as to correspond to a nature of the compound; and
- a chemical equation outputting means that outputs a chemical equation edited by the editing means.

6. The document creation assistance server according to claim 5, wherein
- the editing means edits the compound such that a loop compound, which indicates that a pre-reaction compound and a post-reaction compound are identical, is identifiable.

7. The document creation assistance server according to claim 5, further comprising
- a compound checking means that checks the compound included in the chemical equation obtained by the chemical equation obtaining means against a compound database that stores compound information, wherein
- the editing means edits the compound on the basis of a checking result from the compound checking means.

8. The document creation assistance server according to claim 5, further comprising:
- a notebook checking means that checks a description in the electronic lab notebook data related to each compound included in the chemical equation obtained by the chemical equation obtaining means against a theoretical value obtained from a structural formula of each compound, wherein
- the editing means edits the compound on the basis of a checking result from the notebook checking means.

9. The document creation assistance server according to claim 5, further comprising:
- a selection accepting means that accepts a selection of the compound included in the chemical equation output from the chemical equation outputting means; and
- an operation list outputting means that outputs a list of possible operations in accordance with a nature of the compound accepted by the selection accepting means.

10. The document creation assistance server according to claim 1, further comprising:
- a template storage unit that stores a template with a tag being embedded, wherein
- the document generating means generates the document through a process of embedding the chemical equation obtained by the chemical equation obtaining means into the tag in the template stored in the template storage unit.

11. The document creation assistance server according to claim 1, wherein:
- the document generating means converts the chemical equation into image data and generates the document containing the image data thus converted.

12. A method of assisting with creation of a document that serves as an Example using a computer, comprising:
- accepting, by the computer, identification information that identifies a final product generated through synthesis of a plurality of compounds;
- obtaining, by the computer, a chemical equation for generating the final product corresponding to the identification information accepted, with reference to electronic lab notebook data that electrically describes experiments related to the synthesis of the compounds; and
- generating, by the computer, a document including the chemical equation obtained.

* * * * *